(12) United States Patent
Moaddel et al.

(10) Patent No.: US 6,361,783 B2
(45) Date of Patent: Mar. 26, 2002

(54) COMPOSITIONS CONTAINING STABILIZED ASCORBIC ACID AND RELATED METHODS

(75) Inventors: Teanoosh Moaddel, Appleton, WI (US); William Joseph Radice, New Brunswick, NJ (US); Barbara Ann Wolf, Scarsdale, NY (US); Bernadette Guthauser, North Bergen, NJ (US)

(73) Assignee: Reulon Consumer Products Corporation, New York, NY (US)

( * ) Notice: Subject to any disclaimer, the term of this patent is extended or adjusted under 35 U.S.C. 154(b) by 0 days.

(21) Appl. No.: 09/768,819

(22) Filed: Jan. 25, 2001

Related U.S. Application Data

(60) Continuation of application No. 09/268,159, filed on Mar. 15, 1999, which is a division of application No. 08/883,671, filed on Jun. 27, 1997, now abandoned.

(51) Int. Cl.$^7$ ............................................... A61K 31/34
(52) U.S. Cl. ..................... 424/401; 424/78.03; 514/474; 514/937
(58) Field of Search .............................. 424/401, 78.03; 514/474, 937

(56) References Cited

U.S. PATENT DOCUMENTS 5,587,149 A * 12/1996 Punto et al. .................. 424/59

* cited by examiner

*Primary Examiner*—Jose' G. Dees
*Assistant Examiner*—Michael A. Williamson
(74) *Attorney, Agent, or Firm*—Julie Blackburn

(57) ABSTRACT

A composition in the form of an anhydrous emulsion having as a dispersed phase ascorbic acid dissolved in a nonaqueous polar organic solvent, and as the continous phase a nonaqueous nonpolar organic solvent, as well as a method for dissolving ascorbic acid.

11 Claims, No Drawings

COMPOSITIONS CONTAINING STABILIZED ASCORBIC ACID AND RELATED METHODS

This application is a continuation of Ser. No. 09/268,159 filed Mar. 15, 1999 which is a division of Ser. No. 08/833,671 filed Jun. 27, 1997 now abn.

TECHNICAL FIELD

The invention pertains to the field of compositions, particularly cosmetic compositions, containing ascorbic acid in bioavailable form.

BACKGROUND OF THE INVENTION

It is well known that aging of the skin is due, at least in part, to continual stretching and contraction of both the dermal and epidermal layers of the skin and disruption of the collagen bundles which provide support to the epidermis. Collagen consists of long elastic polypeptide fibers interconnected by bridges which provide the cohesion and stability of connective tissue. This enables collagen to act as an elastic tissue in every direction and retain water. Collagen aging manifests itself as a break in connection between the collagen fibers. Age, severe weather, and pollution accelerate the breaks and slow down renewal of the collagen structure.

Ascorbic acid, or Vitamin C, has many known biological functions. The L-ascorbic acid isomer is biologically active and is known to stimulate the synthesis of collagen, act as a free radical scavenger, and minimize lipid peroxidation and other forms of cellular damage associated with aging.

Ascorbic acid is a white, odorless, crystalline solid having the empirical formula $C_6H_8O_6$, a molecular weight of about 176, and exhibits the following structural formula:

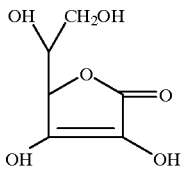

Ascorbic acid is highly soluble, but extremely unstable, in water and rapidly decomposes to form dehydroascorbic acid. This degradation is even more pronounced in the presence of oxygen. It is known that ascorbic acid is much more stable in nonaqueous polar solvents such as polyols, but unfortunately its solubility is limited in such solvents and it generally is thought to be not possible to obtain stable ascorbic acid solutions of more than several percent by weight concentration. Since the anti-aging effects of ascorbic acid are known to be dose-dependent, it is desirable to make stable cosmetic compositions containing ascorbic acid dispersed in a cosmetically acceptable carrier at a concentration of greater than about 5 weight percent, preferably up to 20 or 30 weight percent.

Numerous patents and publications teach various ways of stabilizing ascorbic acid. For example, European Patent Publication No. 0 729 746 teaches an ascorbic acid delivery system comprised of a two compartment kit. In the first compartment is an anhydrous solution of ascorbic acid dissolved in a nonaqueous polar solvent such as a polyol. In the second compartment is an alkaline aqueous solution. The contents of the two compartments are mixed immediately prior to use. The more alkaline aqueous solution increases the pH of the anhydrous ascorbic acid containing solution to provide a composition which does not tingle the skin.

U.S. Pat. No. 5,350,773 teaches stable liquid products used for liquid human and animal food. The compositions are in the form of anhydrous emulsions containing a nonpolar fatty material as the dispersed phase and a polar nonaqueous solvent as the continuous phase. Esters of ascorbic acid are used as the emulsifying agent.

U.S. Pat. No. 5,427,814 teaches a method for protecting a fat against oxidation by mixing ascorbic acid into a polar solvent, and adding the mixture to a heated mixture of tocopherol and lecithin. The polar solvent is then evaporated from the mixture by subjecting the mixture to heat for a period of time.

U.S. Pat. No. 5,308,621 teaches a method for transdermal administration of ascorbic acid. Fine particulate ascorbic acid is suspended in a pharmaceutically acceptable carrier such as a polyol. The compositions are topically applied and the particulate ascorbic acid dissolves upon contact with skin and is absorbed into the skin.

European Patent Publication No. 0 755 674 teaches stabilized ascorbic acid compositions containing a water activity value of less than 0.85. The compositions contain a minimum level of water, in addition to a polyol and an oil.

U.S. Pat. No. 5,587,149 teaches ascorbic acid emulsion compositions comprising ascorbic acid solubilized in a polyol as the dispersed phase and oil as the continuous phase.

However, none of the above patents teach a stable anhydrous ascorbic acid containing composition suitable for cosmetic application where high levels of ascorbic acid are solubilized in the composition and remain stable over protracted periods of time. By "solubilized" it is meant either dissolved or emulsified, but not merely suspended.

An object of the invention is to provide a method for stabilizing ascorbic acid to enable its use in cosmetic products which have anti-aging effects.

Another object of the invention is to provide a stabilized ascorbic acid composition suitable for use in cosmetics.

Another object of the invention is to provide a stabilized ascorbic acid composition containing ascorbic acid at significant concentrations.

Another object of the invention is to provide a stabilized ascorbic acid composition in an anhydrous emulsion form which contains ascorbic acid at significant concentrations.

SUMMARY OF THE INVENTION

The invention comprises a composition in the form of an anhydrous emulsion having as a dispersed phase, ascorbic acid dissolved by means of energy input, in a nonaqueous polar organic solvent, and as the continuous phase a nonaqueous nonpolar organic solvent.

The invention comprises a composition in the form of an anhydrous emulsion having as the dispersed phase a nonaqueous nonpolar organic solvent, and as the continuous phase ascorbic acid dissolved in a nonaqueous polar organic solvent.

The invention is also directed to a method for dissolving ascorbic acid in a nonaqueous polar organic solvent, comprising the steps of:

a) heating the nonaqueous polar organic solvent to a temperature sufficient to dissolve ascorbic acid, b) dissolving particulate ascorbic acid in the heated carrier composition, and c) reducing the temperature of the mixture, preferably to approximately room temperature.

The invention is also directed to a method for making an anhydrous emulsion having as a dispersed phase ascorbic acid dissolved in a nonaqueous polar organic solvent, and as the continuous phase a nonaqueous nonpolar organic solvent, comprising the steps of:

(a) heating the nonaqueous polar organic solvent to a temperature sufficient to dissolve ascorbic acid,
(b) dissolving particulate ascorbic acid in the heated nonaqueous polar organic solvent,
(c) reducing the temperature of the mixture, preferably to approximately room temperature,
(d) emulsifying the ascorbic acid mixture into the nonaqueous nonpolar organic solvent.

The invention also comprises a method for making an anhydrous emulsion having as the dispersed phase a nonaqueous nonpolar organic solvent, and as the continuous phase ascorbic acid dissolved in a nonaqueous polar organic solvent, comprising the steps of:

(a) heating the nonaqueous polar organic solvent to a temperature sufficient to dissolve ascorbic acid,
(b) dissolving particulate ascorbic acid in the heated nonaqueous polar organic solvent,
(c) reducing the temperature of the mixture, preferably to room temperature,
(d) emulsifying the nonaqueous nonpolar organic solvent into the solubilized ascorbic acid mixture.

The invention is directed to cosmetic compositions comprising, by weight of the total composition:

0.1–50% ascorbic acid,
5–98% of a nonaqueous polar organic solvent,
5–98% of a nonaqueous nonpolar organic solvent.

BACKGROUND OF THE INVENTION

Definitions

The term "ascorbic acid" when used in accordance with this invention means L-ascorbic acid, the bioavailable form, and derivatives thereof.

The term "partition coefficient" when used in accordance with the invention means the octanol/water partition coefficient of the solvent as calculated by the ACD/LogP software program marketed by Advanced Chemistry Development, Inc. The software calculates the partition coefficient based upon the molecular structure of the solvent. Actual chemical measurement of partition coefficients may be difficult. The partition coefficient is defined as, in the equilibrium distribution of the solvent between two liquid phases, one of which is water and the other of which is octanol, the ratio of the solvent concentration in the octanol phase to the solvent concentration in the water phase.

The term "polar" means, when used to characterize the solvent, that the logarithm of the octanol/water partition coefficient of the solvent as measured by the ACD/LogP software program, is less than or equal to –0.2 at room temperature. Thus, a polar solvent is one which is capable of solubilizing at least 2 weight percent or more of ascorbic acid at room temperature (generally 25° C.)

The term "nonpolar" means, with respect to the solvent, that the logarithm of the octanol/water partition coefficient of the solvent as measured by the ACD/LogP software program, is greater than –0.2 at room temperature. Thus, a nonpolar solvent is one which is capable of solubilizing less than 2 weight percent of ascorbic acid at room temperature.

The term "anhydrous" means that no substantial amount of water is added to the compositions of the invention. Trace amounts of water (for example, supplied as an impurity in the raw materials used to make the compositions of the invention) may still be present, e.g. in an amount less than about 5% by weight of the total composition, preferably less than 1 to 3% by weight of the total composition.

The term "dissolved" or "dissolving" means that the ascorbic acid is essentially solubilized or dissolved in the nonaqueous polar organic solvent, and that the ascorbic acid will not exist to any appreciable degree in the particulate or crystalline form.

The compositions of the invention may be liquid, semi-solid, or solid at room temperature. The compositions exist in an anhydrous emulsion form. The term "emulsion" is generally used in the cosmetic art to mean water-in-oil or oil-in-water emulsions. However, the compositions of the invention are anhydrous emulsions wherein one anhydrous phase ("the dispersed phase") is dispersed into another anhydrous phase ("the continuous phase"). In the anhydrous emulsions of the invention, the ascorbic acid dissolved into the nonaqueous polar organic solvent forms the dispersed phase. The nonaqueous nonpolar organic solvent forms the continuous phase.

All percentages mentioned herein are percentages by weight unless otherwise indicated.

THE NONAQUEOUS POLAR ORGANIC SOLVENT

The anhydrous emulsions of the invention contain 1–99%, preferably 20–80%, more preferably 40–60% by weight of the total composition, of a nonaqueous polar organic solvent. A variety of nonaqueous polar organic solvents are suitable for use in the dispersed phase of the anhydrous emulsion. As mentioned above, a solvent, in particular a nonaqueous solvent, is considered "polar" in the context of the invention if the logarithm of the partition coefficient of the solvent is less than or equal to –0.2 at room temperature. Examples are as follows.

Polyols

Polyols are suitable nonaqueous polar organic solvents. For purposes of this specification, polyols are defined as compounds which contain three or more hydroxyl groups per molecule. Examples of suitable polyols include fructose, glucamine, glucose, glucose glutamate, glucuronic acid, glycerin, 1,2,6-hexanetriol, hydroxystearyl methylglucamine, inositol, lactose, malitol, mannitol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, riboflavin, sorbeth-6, sorbeth-20, sorbeth-30, sorbeth-40, sorbitol, sucrose, thioglycerin, xylitol, and mixtures thereof. An especially preferred polyol is glycerin.

Polymeric or Monomeric Ethers

Also suitable as the nonaqueous polar organic solvent are homopolymeric or block copolymeric liquid ethers. Polymeric ethers are preferably formed by polymerization of monomeric alkylene oxides, generally ethylene or propylene oxides. Preferred monomeric ethers are those exhibiting the structure below were n=1. Preferred polymeric ethers exhibit the general structure below wherein n=2 to 20:

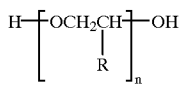

where R is H or $C_{1-10}$ straight or branched chain alkyl, and n is 1 to 20. Examples of such polymeric ethers include PEG, PPG, and derivatives thereof.

Other examples of suitable polymeric ethers include polyoxypropylene polyoxyethylene block copolymers having the general formula:

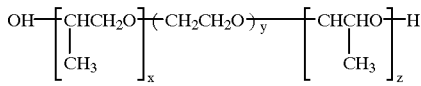

wherein x is 1–200, y is 1–200 and z is 1–200. Such compounds are sold under the CTFA name Meroxapol 105, 108, 171, 172, 174, 178, 251, 252, 254, 255, 258, 311, 312, and 314.

Mono- and Dihydric Alcohols

Also suitable for use as to the nonaqueous polar organic solvent are mono- and dihydric alcohols of the general formula $R(OH)_n$ where n is 1 or 2 and R is a substituted or unsubstituted saturated $C_{2-10}$, preferably $C_{1-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, triethylene glycol, dipropylene glycol, and mixtures thereof.

Sorbitan Derivatives

Sorbitan derivatives, which are defined as ethers or esters of sorbitan, are also suitable polar solvents. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof.

Other nonaqueous polar solvents will also work in the claimed compositions, provided the logarithm of the measured partition coefficient of the solvent is less than –0.2 at room temperature.

THE NONAQUEOUS NONPOLAR ORGANIC SOLVENT

The anhydrous emulsions of the invention contain 1–99%, preferably 20–80%, more preferably 40–60%, by weight of total composition, of a nonaqueous nonpolar organic solvent as the continuous phase. Such solvents are defined as those where the logarithm of the partition coefficient is greater than –0.2 at room temperature. A variety of nonaqueous nonpolar organic solvents can be used in the compositions of the invention.

Silicones

Silicones are suitable nonpolar compounds. The silicones may be volatile or non-volatile. The term "volatile" means that the silicone has a measureable vapor pressure, i.e. a vapor pressure of at least 2 mm. of mercury at 20° C. If volatile, the silicone generally will have a viscosity of 0.5 to 25 centistokes at 25° C. Suitable volatile silicones include cyclic silicones, linear silicones, or mixtures thereof. Cyclic silicones (or cyclomethicones) are of the general formula:

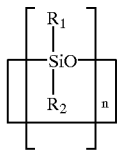

wherein n=3–7, and $R_1$ and $R_2$ are each independently H, $C_{1-8}$ alkyl, aryl, aralkyl, alkenyl, or a cylic or alicylic ring. Preferably $R_1$ and $R_2$ are each independently H or $CH_3$. Most preferably $R_1$ and $R_2$ are each $CH_3$.

Linear volatile silicones in accordance with the invention have the general formula:

$$(CH_3)_3Si-O-[Si(CH_3)_2-O]_n-Si(CH_3)_3$$

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

The silicone may also be nonvolatile, and in particular water insoluble nonvolatile silicones. The term "nonvolatile" means that the silicone has a vapor pressure of less than 2 mm. of mercury at 20° C. A variety of silicones fit this definition including dimethicone, phenyl trimethicone, diphenyl dimethicone, methicone, hexadecyl methicone, stearoxydimethicone, stearyl dimethicone, cetyl dimethicone, and so on.

Cyclomethicone is the preferred silicone for use in the compositions of the invention.

Esters

In addition to the sorbitan esters, other esters are also suitable as the nonaqueous nonpolar organic solvent. In general such esters have the formula RCO—OR wherein each R is independently a $C_{1-25}$ straight or branched chain saturated or unsaturated alkyl, alcylcarbonyloxyalkyl, or alkoxycarbonylalkyl, aryl, which may be substituted or unsubstituted with halogen, hydroxyl, alkyl, and the like.

Examples of suitable esters include alkyl acetates, alkyl behenates, alkyl lactates, alkyl benzoates, alkyl octanoates, alkyl salicylates, and in particular $C_{12-15}$ alkyl benzoate. Examples of the esters are set forth on pages 502–506 of the CTFA Cosmetic Ingredient Handbook, Second Edition, 1992, which is hereby incorporated by reference.

Fats and Oils

Fats and oils are also suitable as the nonaqueous nonpolar organic solvent. Preferably these materials are liquids or semi-solids at room temperature. They are generally defined as glyceryl esters of fatty acids (triglycerides), as well as the synthetically prepared esters of glycerin and fatty acids having the following general formula:

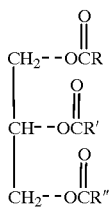

wherein R, R', and R" are each independently fatty acid radicals. Examples of such materials include oils such as apricot kernel oil, avocado oil, canola oil, olive oil, sesame oil, peanut oil, soybean oil, trilinolenin, trilinolein, trioctanoin, tristearin, triolein, sesame oil, rapeseed oil, sunflower seed oil, and so on.

Fat Acids

Fatty acids are also suitable as the nonaqueous nonpolar organic solvent in the compositions of the invention. Preferably the fatty acids are liquid or semi-solid at room temperature. Fatty acids are the carboxylic acids obtained by hydrolysis of animal or vegetable fats and oils. Carboxylic acids having alkyl chains shorter than about seven carbon atoms are not generally considered fatty acids. Fatty acids have the general structure R—COOH where R is a straight or branched chain saturated or unsaturated $C_{7-65}$ alkyl. Examples of suitable fatty acids include arachidic acid, arachidonic acid, behenic acid, capric acid, caproic acid, caprylic acid, coconut acid, corn acid, cottonseed acid, hydrogenated coconut acid, hydroxystearic acid, lauric acid, linoleic acid, linolenic acid, linseed acid, myristic acid, oleic acid, palmitic acid, palm kernel acid, soy acid, tallow acid, and the like.

Fatty Alcohols

Fatty alcohols may also be used as the nonaqueous nonpolar organic solvent. Fatty alcohols are generally made by reducing the fatty acid —COOH group to the hydroxyl function. They generally have the formula $RCH_2OH$. Examples of fatty alcohols are behenyl alcohol, $C_{9-11}$ alcohol, $C_{12-13}$ alcohol, $C_{12-15}$ alcohol, $C_{12-16}$ alcohol, caprylic alcohol, cetearyl alcohol, cetyl alcohol, coconut alcohol, decyl alcohol, lauryl alcohol, myristyl alcohol, oleyl alcohol, and the like.

Hydrocarbons

Hydrocarbons are also good nonaqueous nonpolar organic solvents in accordance with the invention. Examples of suitable hydrocarbons include $C_{7-60}$ isoparaffins, ethane, heptane, hexane, hydrogenated polyisobutene, isobutane, isododecane, isoeicosane, isohexadecane, isopentane, microcrystalline wax, mineral oil, mineral spirits, paraffin, petrolatum, petroleum distillates, squalene, polyethylene, and mixtures thereof. Preferred hydrocarbons are mineral oil and polyethylene.

Lanolin and Lanolin Derivatives

Also suitable as the nonaqueous nonpolar organic solvent are lanolin and derivatives thereof. Examples of such materials include acetylated hydrogenated lanolin, acetylated lanolin alcohol, laneth, lanolin acid, lanolin oil, lanolin alcohol, lanolin wax, and so on.

OTHER INGREDIENTS

It may also be desired to include certain other ingredients in the anhydrous emulsions of the invention, such as surfactants, waxes, colorants, preservatives, and so on.

Surfactants

Silicone Surfactants

The compositions may contain 0.1–15%, preferably 0.5–10%, more preferably 1–8% by weight of the total composition of one or more surfactants. The term "surfactant" is defined, in accordance with the invention, as a compound having at least one hydrophilic moiety and at least one lipophilic moiety. The surfactants may be silicone surfactants (also referred to as organosiloxane emulsifiers) or organic surfactants.

Suitable silicone surfactants used in the compositions of the invention may be liquid or solid at room temperature and are generally a water-in-oil or oil-in-water type surfactants which are preferably nonionic, having an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

Another method of calculating HLB is:

$$HLB = 20(1 - S/A)$$

where S is the saponification number of the surfactant and A is the acid number of the surfactant.

The silicone surfactant or emulsifier used in the compositions of the invention is a polymer containing a polymeric backbone including repeating siloxy units that may have cyclic, linear or branched repeating units, e.g. di(lower) alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organo-compatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof. The $C_{1-40}$ alkyl may be non-interrupted, or interruped by one or more oxygen atoms, a benzene ring, amides, esters, or other functional groups.

The polymeric organosiloxane emulsifier used in the invention may have any of the following general formulas:

$M_xQ_y$, or $M_xT_y$, or $MD_xD'_yD''_zM$ wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RSiO_{1.5}$ or $RSiO_{1.5}$. Q is a quadrifunctional siloxy unit having the empirical formula $SiO_2$, and D, D', D", x, y, and z are as set forth below, with the proviso that the compound contains at least one hydrophilic radical and at least one lipophilic radical. Examples of emulsifiers used in the compositions of the invention are of the general formula:

$MD_xD'_yD''_zM$ wherein the trimethylsiloxy endcap unit is unsubstituted or mono-substituted, wherein one methyl group is substituted with a lipophilic radical or a hydrophilic radical. Examples of such substituted trimethylsiloxy endcap units include $(CH_3)_2HPSiO$, $(CH_3)_2LPSiO$, $(CH_3)_2CH_2HPSiO$, $(CH_3)_2CH_2LPSiO$, wherein HP is a hydrophilic radical and LP is a lipophilic radical. D, D', and D" are difunctional siloxy units substituted with methyl, hydrogen, a lipophilic radical, a hydrophilic radical or mixtures thereof. In this general formula:

x=0–5000, preferably 1–1000 y=0–5000, preferably 1–1000, and z=0–5000, preferably 0–1000, with the proviso that the compound contains at least one lipophilic radical and at least one hydrophilic radical. Examples of these polymers are disclosed in U.S. Pat. No. 4,698,178, which is hereby incorporated by reference. Particularly preferred is a linear silicone of the formula:

$MD_xD'_yD''_zM$ wherein $M=RRRSiO_{1/2}$

D and $D'=RR'SiO_{2/2}$ $D''=RRSiO_{2/2}$ x, y, and z are each independently 0–1000,
where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy $D=Si[(CH_3)][(CH_2)_nCH_3]O_{2/2}$ where n=1–40, $D'=Si[(CH_3)][(CH_2)_o—O—PE)]O_{2/2}$ where PE is $(—C_2H_4O)_a(—C_3H_6O)_bH$, o=0–40, a=1–100 and b=1–100, and $D''=Si(CH_3)_2O_{2/2}$ Typical examples of preferred organosiloxane emulsifiers in accordance with the invention include those set forth below:

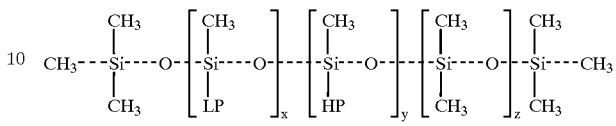

I.

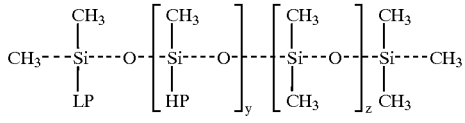

II.

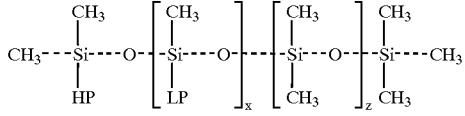

III.

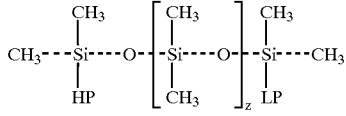

IV.

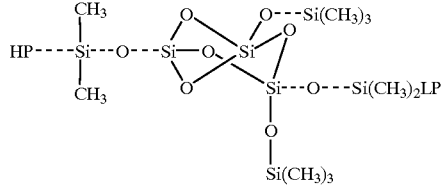

V.

wherein LP is a lipophilic radical
HP is a hydrophilic radical
x is 0–5000
y is 0–5000, and
z is 0–5000, with the proviso that the organosiloxane contains at least on hydrophilic radical and at least one lipophilic radical. More preferred are compounds of the generic formula I wherein LP is a lipophilic radical which is a $C_{1-40}$ straight or branched chain alkyl, HP is a hydrophilic radical containing hydroxy-polyethyleneoxy, and z is at least 1. Most preferred is a compound of the formula:

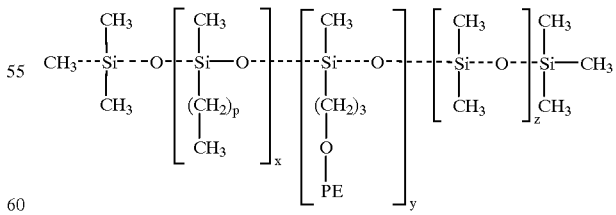

wherein p is 10–40, preferably 12–20, most preferably 15, and

PE is $(—C_2H_4O)_a(—C_3H_6O)_b—H$ where x, y, z, a, and b are such that the maximum molecular weight of the polymer is approximately 50,000. Organosiloxane polymers useful in the compositions of the invention are commercially available from Goldschmidt Corporation under the ABIL tradename. The preferred polymer is cetyl dimethicone copolyol and has the tradename ABIL WE 09 or ABIL WS 08. The cetyl dimethicone copolyol may be used alone or in conjunction with other non-silicone organic emulsifiers. Preferred is where the cetyl dimethicone copolyol is in an admixture with other non-silicone organic emulsifiers and emollients. In particular, blends of 25–50% of the organosiloxane emulsifier, 25–50% of a non-silicone organic emulsifier, and 25–50% by weight emollients or oils are preferred. For example, the mixtures identified by the C.T.F.A. names cetyl dimethicone copolyol (and) polyglyceryl 4-isostearate (and) hexyl laurate, or cetyl dimethicone copolyol (and) polyglyceryl-3 oleate (and) hexyl laurate both work well. These blends contain approximately 25–50% of each ingredient, for example ABIL WE 09 contains approximately, by weight of the total ABIL composition, 25–50% cetyl dimethicone copolyol, 25–50%, polyglyceryl 4-isostearate, and 25–50% of hexyl laurate which is an emollient or oil.

Another type of preferred organosiloxane emulsifier suitable for use in the compositions of the invention are emulsifiers sold by Union Carbide under the Silwet™ trademark. These emulsifiers are represented by the following generic formulas:

wherein PE=—(EO)$_m$(PO)$_n$R

R=lower alkyl or hydrogen

Me=methyl

EO is polyethyleneoxy

PO is polypropyleneoxy m and n are each independently 1–5000 x and y are each independently 0–5000, and

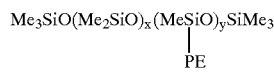

wherein PE=—CH$_2$CH$_2$CH$_2$O(EO)$_m$(PO)$_n$Z

Z=lower alkyl or hydrogen, and

Me, m, n, x, y, EO and PO are as described above, with the proviso that the molecule contains a lipophilic portion and a hydrophilic portion. Again, the lipophilic portion can be supplied by a sufficient number of methyl groups on the polymer backbone.

Particularly preferred is a Silwet™ polymer of the following general formula:

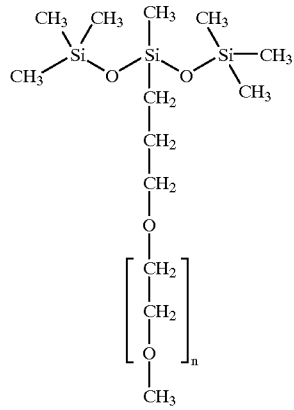

Wherein n is 1–10, preferably 8.

Another preferred organosiloxane emulsifier for use in the compositions of the invention is dimethicone copolyol.

Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane emulsifiers sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2–5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusofi, those sold by Hoechst under the tradename Arkophob, are also suitable for use in the invention.

Also suitable as surfactants are various organic surfactants such as anionic, nonionic, amphoteric, zwitterionic, or cationic surfactants.

The compositions of the invention comprise 0.5–20%, preferably 0.5–15%, more preferably 0.5–10%, of a surfactant. Suitable surfactants may be anionic, nonionic, amphoteric, or zwitterionic.

Anionic Surfactants

Anionic surfactants include alkyl and alkyl ether sulfates generally having the formula ROSO$_3$M and RO(C$_2$H$_4$O)$_x$SO$_3$M wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

wherein R$_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-Noctadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sulfones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

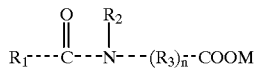

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Nonionic Surfactants

The composition can contain one or more nonionic surfactants. Nonionic surfactants are generally compounds produced by the condensation of alkylene oxide groups with a hydrophobic compound. Classes of nonionic surfactants are:

(a) Long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety.

(b) Polysorbates, such as sucrose esters of fatty acids. Examples of such materials include sucrose cocoate, sucrose behenate, and so on.

(c) Polyethylene oxide condensates of alkyl phenols, for example the condensation products of alkyl phenols having an alkyl group of 6 to 20 carbon atoms with ethylene oxide being present in amounts of about 10 to 60 moles of ethylene oxide per mole of alkyl phenol.

(d) Condensation products of ethylene oxide with the reaction product of propylene oxide and ethylene diamine.

(e) Condensation products of aliphatic alcohols having 8 to 18 carbon atoms with ethylene oxide, for example a coconut alcohol/ethylene oxide condensate having 10 to 30 moles of ethylene oxide per mole of coconut alcohol, the coconut alcohol fraction having 10 to 14 carbon atoms.

(f) Long chain tertiary amine oxides such as those corresponding to the general formula:

$R_1R_2R_3NO$ wherein $R_1$ contains an alkyl, alkenyl or monohydroxyalcyl radical ranging from about 8 to 18 carbon atoms in length, from 0 to about 10 ethylene oxide moieties, and from 0 to about 1 glyceryl moiety and $R_2$ and $R_3$ are each alkyl or monohydroxyalkyl groups containing from about 1 to about 3 carbon atoms.

(g) Long chain tertiary phosphine oxides corresponding to the general formula:

$RR_1R_2PO$ wherein R contains an alkyl, alkenyl, or monohydroxyalkyl radical having 8 to 18 carbon atoms, from 0–10 ethylene oxide moieties and 0 or 1 glyceryl moiety, and $R_2$ and $R_3$ are each alkyl or monohydroxyalkyl group containing from about 1 to 3 carbon atoms.

(h) Alkyl polysaccharides having a hydrophobic group of 6 to 30, preferably 10, carbon atoms and a polysaccharide group such as glucose, galactose, etc. Suitable alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on.

(i) Polyethylene glycol (PEG) glyceryl fatty esters, having the formula $RC(O)OCH_2CH(OH)CH_2(OCH_2CH2)_nOH$ wherein n is 5–200 and RC(O)— is a hydrocarbylcarbonyl group wherein R is preferably an aliphatic radical having 7 to 19 carbon atoms.

(j) Other nonionic surfactants that may be used include $C_{10-18}$ alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

Amphoteric Surfactant

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may be imidazolinium compounds having the general formula:

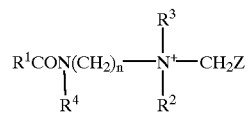

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or CH$_2$CH$_2$OCH$_2$CHCOOM; R$^4$ is hydrogen, CH$_2$CH$_2$OH, or CH$_2$CH$_2$OCH$_2$CH$_2$COOM, Z is CO$_2$M or CH$_2$CO$_2$M, n is 2 or 3, preferably 2, M is hydrogen, a cation such as an alkali metal, alkaline earth metal, ammonium, or alkanol ammonium. cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula

R—NH(CH$_2$)$_n$COOM or iminodialkanoates of the formula:

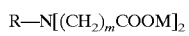

R—N[(CH$_2$)$_m$COOM]$_2$ and mixtures thereof; wherein n and m are 1 to 4, R is C$_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-iminodipropionic acid, or mixtures thereof.

Zwitterionic surfactants are also suitable for use in the compositions of the invention. The general formula for such surfactants is:

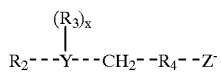

R$_2$- - -Y- - -CH$_2$- -R$_4$- -Z$^-$ wherein R$_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; R$_3$ is an alkyl or monohydroxyalkyl group containing about 1 to 3 carbon atoms; X is 1 when Y is a sulfur atom, and 2 when Y is a nitrogen or phosphorus atom; R$_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionics include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido- betaines such as coco dimethyl sulfopropyl betaine, stearyl dimethyl sulfopropyl betaine, and the like.

Cationic surfactants and/or polymers may be incorporated into the compositions of the invention. If so, 0.01–15%, preferably 0.05–10%, preferably 0.10–8% of a cationic ingredients is suggested. Suitable cationic ingredients include cationic polymers, quaternary ammonium salts, or the salts of fatty amines. Quaternary ammonium salts have the formula:

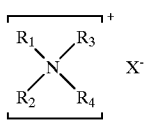

wherein R$_1$ is hydrogen, an aliphatic group of 1 to 22 carbon atoms, or aromatic, aryl, or alkaryl group having 12 to 22 carbon atoms; R$_2$ is an aliphatic group having 1–22 carbon atoms; R$_3$ and R$_4$ are each alkyl groups of from 1 to 3 carbon atoms, and X is an anion selected from halogen, acetate, phosphate, nitrate and methyl sulfate radicals. The aliphatic groups may contain, in addition to carbon and hydrogen atoms, ether linnages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, dicetyldimonium chloride, and mixtures thereof.

Other quaternary ammonium salts useful as the cationic surfactant are compounds of the general formula:

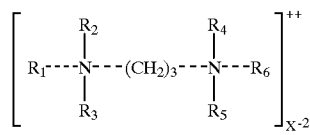

wherein R$_1$ is an aliphatic group having 16 to 22 carbon atoms, R$_2$, R$_3$, R$_4$, R$_5$, and R$_6$ are the same or different and are selected from H and alkyls having 1 to 4 carbon atoms and X is an anion as above defined.

Also, quaternary imidazolinium salts having the following general formula are also suitable:

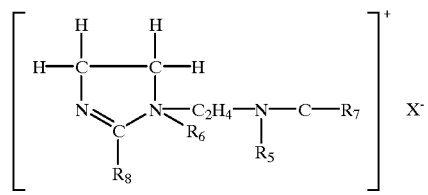

wherein R$_5$ is hydrogen or a C$_{1-4}$ alkyl; R$_6$ is a C$_{1-4}$ alkyl; R$_7$ is a C$_{8-22}$ alkyl; and R$_8$ is hydrogen, or a C$_{1-22}$ alkyl; and X is an anion as defined above.

Also suitable as the cationic surfactant are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

Also suitable as the cationic ingredient are cationic polymers such as:

(a) Quaternary derivatives of cellulose ethers such as polymers sold under the tradename JR-125, JR-400, JR-30M. Preferred is Polyquaternium 10, which is a polymeric quaternary ammonium salt of hydroxyethyl cellulose reacted with a trimethyl ammoniun subsituted epoxide.

(b) Copolymers of vinylpyrrolidone having monomer units of the formula:

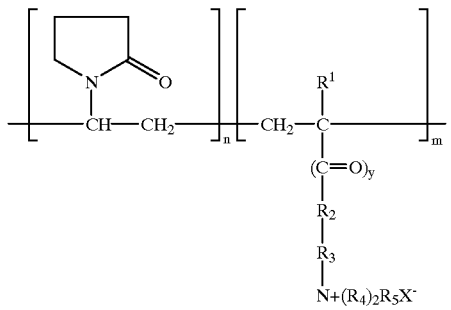

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—CHOH—$CH_2$—, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

(c) Homopolymer of dimethyldiallylammonium chloride, or copolymer of dimethyldiallylammonium chloride and acrylamide. Such compounds are sold under the tradename MERQUATT™ by Merck and Company.

(d) Homopolymers or copolymers derived from acrylic or methacrylic acid wherein the monomer units are selected from the group consisting of acrylamide, methylacrylamide, diacetone-acrylamide, acrylamide or methacrylamide substituted on the nitrogen by lower alkyl, alkyl esters of acrylic acid and methacrylic acid, vinylpyrrolidone, and vinyl esters.

Examples of cationic polymers that can be used in the compositions of the invention are the cationic polymers disclosed in U.S. Pat. Nos. 5,240,450 and 5,573,709, which are hereby incorporated by reference.

Waxes

The compositions of the invention may contain 0.1–25%, preferably 0.5–20%, more preferably 1–15% by weight of the total composition of wax. Suitable waxes have a melting point of 35 to 120° C., and can be animal waxes, plant waxes, mineral waxes, silicone waxes, synthetic waxes, and petroleum waxes. Examples of waxes in accordance with the invention include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, thylene homo- or copolymers, stearoxy dimethicone, dimethicone behenate, stearyl dimethicone, and the like, as well synthetic homo- and copolymer waxes such as PVP/eicosene copolymer, PVP/hexadecene copolymer, and the like.

Branched Chain Silicone Resins

It may be desireable to include one or more branched chain silicone resins in the compositions of the invention. If so, a range of 0.001–20%, preferably 0.01–15%, more preferably 0.1–10% by weight of the total composition is suggested. Examples of suitable silicone resins include siloxy silicate polymers having the following general formula:

$$[(RR'R'')_3SiO_{1/2}]_x[SiO_2]_y$$

wherein R, R' and R'' are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R'' are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40–60% volatile silicone and 40–60% trimethylsiloxy silicate. Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

Other branched chain silicone resins are silicone esters comprising units of the general formula $R_aR^E{}_bSiO_{[4-(a+b)/2]}$ or $R^{13}{}_xR^E{}_ySiO_{1/2}$, wherein R and $R^{13}$ are each independently an organic radical such as alkyl, cycloalkyl, or aryl, or, for example, methyl, ethyl, propyl, hexyl, octyl, decyl, aryl, cyclohexyl, and the like, a is a number ranging from 0 to 3, b is a number ranging from 0 to 3, a+b is a number ranging from 1 to 3, x is a number from 0 to 3, y is a number from 0 to 3 and the sum of x+y is 3, and wherein $R^E$ is a carboxylic ester containing radical. Preferred $R_E$ radicals are those wherein the ester group is formed of one or more fatty acid moieties (e.g. of about 6, often about 6 to 30 carbon atoms) and one or more aliphatic alcohol moieties (e.g. of about 10 to 30 carbon atoms). Examples of such acid moieties include those derived from branched-chain fatty acids such as isostearic, or straight chain fatty acids such as behenic. Examples of suitable alcohol moieties include those derived from monohydric or polyhydric alcohols, e.g. normal alkanols such as n-propanol and branched-chain etheralkanols such as (3,3,3-trimethylolpropoxy)propane. Preferably the ester subgroup (i.e. the group containing the carboxylic ester) will be linked to the silicon atom by a divalent aliphatic chain that is at least 2 or 3 carbon atoms in length, e.g. an alkylene group or a divalent alkyl ether group. Most preferably that chain will be part of the alcohol moiety, not the acid moiety. More particularly, the cross-linked silicone ester can be a liquid or solid at room temperature. Preferably it will have a waxy feel and a molecular weight of no more than about 100,000 daltons.

Such silicone resins having the above formula are disclosed in U.S. Pat. No. 4,725,658 and U.S. Pat. No. 5,334,737, which are hereby incorporated by reference. These ingredients are commercially available from General Electric under the tradenames SF 1318 and SF 1312, respectively.

Pigments and Powders

The composition of the invention may contain 0.001–35%, preferably 0.01–20% more preferably 0.1–10%, by weight of the total composition, of dry particulate matter having a particle size of 0.02 to 200, preferably 0.5 to 100, microns. The particulate matter may be colored or non-colored (for example white). Suitable powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecitin, amino acids, mineral oil, silicone oil or various other agents either alone or in combination, which coat the powder surface and render the particles more lipophilic in nature.

The powder component also may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultamarines, chromium, chromium hydroxide colors, and mixtures thereof.

The composition may contain a mixture of both pigmented and non-pigmented powders. The percentage of pigments used in the powder component will depend on the type of cosmetic being formulated.

Sunscreens

The compositions of the invention may contain 0.001–20%, preferably 0.01–10%, more preferably 0.05–8% of one or more sunscreens. A sunscreen is defined as an ingredient that absorbs at least 85 percent of the light in the UV range at wavelengths from 290 to 320 nanometers, but transmit UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on page 582 of the *CTFA Cosmetic Ingredient Handbook*, Second Edition, 1992, as well as U.S. Pat. No. 5,620,965, both of which are hereby incorpated by reference. Examples of such sunscreen materials are p-aminobenzoic acid (PABA), cinoxate, diethanolamine p-methoxycinnamate (DEA-methoxycinnamate), Digalloyl trioleate, dioxybenzone (Benzophenone-8), ethyl 4-[bis-(hydroxypropyl)] aminobenzoate (ethyl dihydroxypropyl PABA), 2-ethylhexyl-2-cyano-3,3-diphenylacrylate (octocrylene), ethylhexyl p-methoxycinnamate (Octyl methoxycinnamate), 2-ethylhexyl salicylate (Octyl salicylate), glyceryl aminobenzoate (Glyceryl PABA), homosalate, lawsone with dihydroxyacetone, menthyl anthranilate, oxybenzone (Benzophenone-3), Padimate A (Pentyl Dimethyl PABA), Padimate O, (Octyl Dimethyl PABA), 2-Phenylbenzimidazole-5-sulfonic acid (Phenylbenzimidazole Sulfonic acid), Red Petrolatum, Sulisobenzone (Benzophenone-4), triethanolamine salicylate (TEA-Salicylates), and so on.

Preservatives

The composition may contain 0.0001–8%, preferably 0.0016%, more preferably 0.005–5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, ocresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference.

The compositions of the invention may contain vitamins and/or coenzymes, as well as antioxidants. If so, 0.001–10%, preferably 0.01–8%, more preferably 0.05–5% by weight of the total composition are suggested. Suitable vitamins include the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

Alpha or Beta Hydroxy Acids, Alpha Keto Acids

It may be desired to add one or more alpha or beta hydroxy acids or alpha ketoacids to the compositions of the invention. Suggested ranges are 0.01–20%, preferably 0.1–15%, more preferably 0.5–10% by weight of the total composition. Suitable alpha hydroxy acids and alpha ketoacids are disclosed in U.S. Pat. No. 5,091,171, which is hereby incorporated by reference. Such alpha hydroxy acids are as follows:

a) Organic carboxylic acids where one hydroxyl group is attached to the alpha carbon atom of the acid. The general structure of such alpha hydroxy acids may be represented by the following formula:

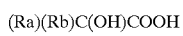

(Ra)(Rb)C(OH)COOH wherein Ra and Rb are H, F, Cl, Br, alkyl, aralkyl, or aryl group of saturated, unsaturated, straight or branched chain or cyclic form having 1–10 carbon atoms, and in addition Ra or Rb may carry OH, CHO, COOH and alkoxy groups having 1 to 9 carbon atoms.

The second group of alpha hydroxy acids may be represented by the following formula:

(Ra)COCOO(Rb)

wherein Ra and Rb are H, alkyl, aralkyl, or aryl groups of straight or branched chain saturated or unsaturated alkyl having 1 to 10 carbon atoms, and in addition Ra may carry F, Cl, Br, I, OH, CHO, COOH, and alkoxy groups having 1 to 10 carbon atoms.

The alpha hydroxy acids may exist in the keto acid form, or the ester form. Examples of such alpha hydroxy acids include glycolic acid, malic acid, pyruvic acid, mandelic acid, lactic acid, methyllactic acid, and so on.

Also beta hydroxy acids such as salicylic acid, and derivatives thereof may be included in the compositions of the invention.

THE METHOD

The anhydrous emulsions of the invention are made by first subjecting the nonaqueous polar organic solvent to an input of energy, preferably heat energy. In particular, the nonaqueous polar organic solvent is heated to a temperature sufficient to dissolve the ascorbic acid. A temperature above room temperature is generally required to achieve solubilization of ascorbic acid to any appreciable degree. Preferably, the nonaqueous polar organic solvent is heated to a temperature of about 70 to 170, more preferably about 80 to 120, more preferably about 90–110, and most preferably about 95–105° C. The heat energy required may depend on conditions such as the pressure at which the nonaqueous polar organic solvent is maintained. For example, if the pressure of the nonaqueous polar organic solvent is increased above standard pressure at room temperature, the temperature required to dissolve appreciable levels of ascorbic acid in the solvent is correspondingly less. Conversely, if the nonaqueous polar organic solvent is maintained at a pressure which is less than the standard pressure at room temperature, the temperature required to dissolve appreciable levels of ascorbic acid may be correspondingly greater. The energy source may be standard heat as well as heat radiation from sources such as long and short microwaves, infrared radiation, sonication, microfluidization, and the like.

While maintaining the temperature, the ascorbic acid is added to the nonaqueous polar organic solvent with stirring until dissolved. The temperature of the mixture is then reduced, i.e. the mixture is cooled, by reducing the temperature by 10 to 145° C., more preferably by 20 to 100° C., most preferably by 40 to 95° C. Most preferably the mixture is cooled to room temperature. It is preferred to cool the mixture to room temperature quickly, for example by plunging a container of the mixture into an ice water bath until the mixture attains room temperature.

In the preferred embodiment of the invention, one of the nonaqueous polar organic solvents is heated in a vessel to about 100° C. The ascorbic acid is added with stirring until dissolved. The vessel containing the mixture is then plunged into an ice water bath and held there until it has cooled to room temperature. Then, the mixture is reheated to a temperature of 70–170°, 80–110°, preferably 95–105°, more preferably about 100° C. and the second nonaqueous polar organic solvent is added with stirring. The mixture is then rapidly cooled to room temperature by putting it into an ice water bath.

It has been discovered that the rapid cooling appears to promote solubilization of the ascorbic acid into the nonaqueous polar organic solvent. In addition, adding the nonaqueous polar organic solvents one at a time followed by rapid cooling, promotes the highest level of stability and solubility of ascorbic acid in the nonaqueous polar organic solvent. Most unexpectedly, concentrations of solubilized ascorbic acid up to 25% have been achieved using solvents which normally provide very low solubility of ascorbic acid.

The ascorbic acid solubilized in the nonaqueous polar organic solvent is emulsified into the nonaqueous nonpolar organic solvent at room temperature by homogenizing by using standard homogenizing equipment such as the Eppenbach Homo-mixer. In the case where the ascorbic acid dissolved in the nonaqueous polar organic solvent forms the continuous phase, the nonaqueous nonpolar organic solvent is emulsified into the ascorbic acid mixture at room temperature using homogenization.

EXAMPLE 1

An anhydrous emulsion suitable as a skin lotion, was made in accordance with the invention as follows:

| | w/w % |
|---|---|
| Cetyl dimethicone copolyol | 3.00 (surfactant) |
| Hydrogenated castor oil | 5.00 (wax) |
| Polyethylene | 1.00 (wax) |
| Polyglyceryl-4-isostearate | 1.50 (surfactant) |
| Polyethylene/mineral oil (6:94) | 15.00 (wax/nonpolar organic solvent) |
| Cyclomethicone | 12.00 (nonpolar organic solvent) |
| $C_{12-15}$ alkyl benzoate | 12.50 (nonpolar organic solvent) |
| Glycerine | 33.40 (polar organic solvent) |
| PEG-6 | (6.70 polar organic solvent) |
| Ascorbic acid | 10.00 |

The glycerine was heated to a temperature of 100° C. The ascorbic acid was added to the glycerine while maintaining the temperature at 100° C., while stirring until dissolved. The solution was then put into an ice water bath until the mixture cooled to room temperature. The mixture was a clear solution. The mixture was then heated back up to 100° C., and the PEG-6 was added to the hot mixture with stirring. The mixture was then put into an ice water bath again until cooled to room temperature.

The remaining ingredients were separately mixed, yielding a nonpolar solvent phase, and the ascorbic acid/glycerine/PEG-6 mixture was dispersed into the nonpolar solvent phase by homogenizing using an Eppenbach Homo-mixer.

EXAMPLE 2

An anhydrous emulsion suitable for use as a skin lotion was made as follows:

| | w/w % |
|---|---|
| Dimethicone copolyol/cyclomethicone (10:90) | 10.50 (surfactant/nonpolar organic solvent) |
| Cetyl dimethicone copolyol | 1.00 (surfactant) |
| Trihydroxystearin/cyclomethicone (17.5:82.5) | 9.50 (nonpolar organic solvent/nonpolar organic solvent) |
| Dimethiconol/cyclomethicone (13:87) | 2.00 (surfactant/nonpolar organic solvent) |
| PEG-6 | 31.00 (polar organic solvent) |
| Glycerin | 35.40 (polar organic solvent) |
| Ascorbic acid | 10.60 |

The glycerin was heated to a temperature of 100° C. The ascorbic acid was added to the heated mixture while maintaining the temperature at 100° C., and stirring until dissolved. The mixture was then put into an ice water bath until the mixture cooled to room temperature. The mixture was then heated back up to 100° C., and the PEG-6 was added to the hot mixture with stirring. The mixture was then put into an ice water bath until cooled to room temperature.

The remaining ingredients were separately mixed, and the ascorbic acid/glycerine/PEG-6 mixture was dispersed into the nonpolar phase by homogenizing.

EXAMPLE 3

Anhydrous emulsions suitable for use as a skin treatment lotion and cream were prepared as follows:

|  | 1 | 2 |
|---|---|---|
| Ascorbic acid | 10.00 | 10.00 |
| PEG-6 (nonaqueous polar organic solvent) | 33.7 | 6.7 |
| Glycerine (nonaqueous polar organic solvent) | 33.3 | 33.3 |
| Octyl methoxycinnamate (sunscreen) | 7.5 | — |
| Safflower oil (nonaqueous nonpolar organic solvent) | 7.5 | — |
| Tocopheryl acetate (vitamin) | 1.0 | — |
| Polyacrylamide/C13-14 isoparaffin/laureth-7 | 1.0 | — |
| Sorbitan oleate (surfactant) | 2.7 | — |
| Polysorbate 80 (nonaqueous polar organic solvent) | 3.3 | — |
| Steareth-21 (surfactant) | — | 12.0 |
| Steareth-2 (surfactant) | — | 4.0 |
| Polysorbate 20 (nonaqueous polar organic solvent) | — | 1.0 |
| Glyceryl stearate (nonaqueous nonpolar organic solvent) | — | 8.0 |
| Cetyl alcohol (nonaqueous nonpolar organic solvent) | — | 4.0 |
| C12-15 alkyl benzoate | — | 16.6 |
| Preservatives | — | 0.4 |

The glycerine was heated to a temperature of 100° C. The ascorbic acid was added to the heated mixture while maintaining the temperature at 100° C., and stirring until dissolved. The mixture was then put into an ice water bath until the mixture cooled to room temperature. The mixture was then heated back up to 100° C., and the PEG-6 was added to the hot mixture with stirring. The mixture was then put into an ice water bath until cooled to room temperature.

The remaining ingredients were separately mixed, and dispersed into the ascorbic acid/glycerine/PEG-6 mixture by homogenizing. Sample 1 provided a pourable translucent gel-like emulsion. Sample 2 provided a non-pourable opaque cream.

EXAMPLE 4

The solubility of ascorbic acid in various solvents was correlated with the octanol/water partition coefficient of the solvent. The partition coefficient of each solvent was measured using a software program marketed by Advanced Chemistry Development, Inc., called the ACD/LogP program, which calculates the partition coefficient from the molecular structure of the solvent. The solubility of the ascorbic acid was determined by heating the solvent to a temperature in excess of 100° C., preferably in the range of 105 to 110° C. while monitoring with a thermometer. Measured amounts (in weight percent, i.e. 1%, 2%, 3%, 4%, 5%, up to 20%, 25%, etc.) of ascorbic acid were added to separate tubes containing the hot solvent while mixing. After the ascorbic acid dissolved, the samples were cooled to room temperature. The solubility of ascorbic acid in the particular solvent was the maximum weight percent of ascorbic acid that could be solubilized in the solvent before the solution turned cloudy and crystal formation occurred at room temperature after one month. In other words, the solubility was determined to be the maximum weight percent of ascorbic acid that could be solubilized in the solvent, where the solution remained clear and no microscopic evidence of crystal formation was evident at room temperature after one month.

The results are set forth below:

| Solvent | Ascorbic Acid Solubility wt % | LogP |
|---|---|---|
| Ethylene glycol | 25 | −1.69 |
| 1,2-propanediol | 17 | −1.34 |
| 1,2-butanediol | 9 | −0.81 |
| 1,2-pentanediol | 3 | −0.28 |
| 1,2-hexanediol | 1 | 0.25 |
| Diethylene glycol | 21 | −1.51 |
| Triethylene glycol | 17 | −1.50 |
| Glycerine | 17 | −2.41 |
| Polyethylene glycol 300 | 8 | −1.46 |
| Polyethylene glycol 400 | 7 | −1.43 |
| Polyethylene glycol 600 | 5 | −1.39 |
| Dipropylene glycol | 9 | −0.82 |
| Polypropylene glycol n = 6 | 3 | 0.97 |
| Polyglycol EP530 | 0.1 | 9.25 |
| Synalox PB-200 fluid (n = 14) | 0.5 | 5.79 |
| Glyceryl monooleate | 0.1 | 6.91 |
| Glyceryl stearate | 0.1 | 7.43 |
| Diglycerol | 18 | −2.86 |

The solvents which exhibit octanol/water partition coefficients of less than −0.2 may be used as the nonaqueous polar organic solvent. The solvents which exhibit octanol/water partition coefficients of greater than −0.2 may be used as the nonaqueous nonpolar organic solvent.

EXAMPLE 5

Stability studies were performed on the formula of Example 2, containing 10.6% ascorbic acid, as follows:

| Time | Temperature | % Ascorbic Acid Remaining |
|---|---|---|
| 5 months | 25° C. | 9.6% |
| 5 months | 40° C. | 9.6% |
| 5 months | 50° C. | 6.6% |

It can be seen that the ascorbic acid in the formula of Example 2 exhibits good stability at room temperature and at elevated temperatures.

While the invention has been described in connection with the preferred embodiment, it is not intended to limit the scope of the invention to the particular form set forth, but, on the contrary, it is intended to cover such alternatives, modifications and equivalents as may be included within the spirit and scope of the invention as defined by the appended claims.

We claim:

1. A method for dissolving ascorbic acid in nonaqueous polar organic solvent comprising a mixture of a polyol having three or more carbon atoms and an ingredient having the formula:

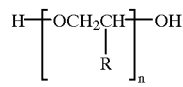

wherein R is H, and n is 2 to 10, comprising the steps of:
 a) heating the polyol to a temperature of 70 to 170° C.,
 b) dissolving ascorbic acid in the polyol,
 c) rapidly cooling the mixture, d) reheating the mixture to a temperature of 70 to 170° C.,
e) adding the ingredient having the formula,

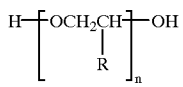

wherein R is H, and n is 2 to 10,
f) rapidly cooling the mixture.

2. The method of claim 1 wherein the composition is cooled to room temperature.

3. The method of claim 1 wherein the polyol is glycerine.

4. The method of claim 1 wherein the ingredient is PEG-1 through PEG-10.

5. The method of claim 4 wherein the ingredient is PEG-6.

6. A method for making an anhydrous emulsion having as a dispersed phase ascorbic acid dissolved in a nonaqueous polar organic solvent which is a mixture of a polyol having three or more carbon atoms and an ingredient having the formula:

wherein R is H, and n is 2 to 10, and as the continuous phase a nonaqueous nonpolar organic solvent which is a silicone, said composition comprising, by weight of the total composition:

0.1–40% ascorbic acid,
5–98% of the nonaqueous polar organic solvent,
5–98% of the silicone, comprising the steps of:
  a) heating the polyol to a temperature of about 70 to 120° C.,
  b) dissolving particulate ascorbic acid in the heated polyol composition,
  c) rapidly cooling the mixture
  d) reheating the mixture to a temperature of about 70 to 120° C.
  e) adding the ingredient having the formula:

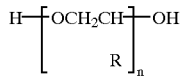

wherein R is H, and n is 2 to 10,
  f) rapidly cooling the mixture,
wherein the amount of ascorbic acid solubilized in the cooled mixture after practice of the method comprised of steps a through f is greater than the amount of ascorbic acid that would be soluble in the nonaqueous polar organic solvent prior to practice of the method comprised of steps a through f; and
  g) emulsifying the composition into the silicone oil.

7. The method of claim 6 wherein the silicone is selected from the group consisting of dimethicone, dimethicone copolyol, cetyl dimethicone copolyol, and mixtures thereof.

8. The method of claim 7 wherein the silicone is dimethicone, dimethicone copolyol, or mixtures thereof.

9. The method of claim 7 wherein the nonaqueous polar organic solvent is glycerine.

10. The method of claim 7 wherein the nonaqueous polar organic solvent is PEG-6.

11. The method of claim 6 wherein the polyol is glycerine and the ingredient is PEG-6.

* * * * *